United States Patent
Villax et al.

(10) Patent No.: US 6,469,208 B1
(45) Date of Patent: Oct. 22, 2002

(54) PROCESS FOR THE PREPARATION OF CRYSTALLINE AND SOLVENT FREE IOHEXOL

(75) Inventors: Guido Du Boulay Villax, Ilha Da Taipa (MO); Alexandre Jose Ganchas De Carvalho, Vila Franca de Xira (PT); Carlos Manuel Alvarez Perez, Lisbon (PT)

(73) Assignee: Hovione Inter Ltd. (CH)

( * ) Notice: Subject to any disclaimer, the term of this patent is extended or adjusted under 35 U.S.C. 154(b) by 571 days.

(21) Appl. No.: 08/964,339

(22) Filed: Nov. 4, 1997

(51) Int. Cl.[7] ............................................. C07C 233/22
(52) U.S. Cl. ..................... 564/153; 564/152; 424/9.454
(58) Field of Search ................................ 564/153, 152; 424/9.454

(56) References Cited

U.S. PATENT DOCUMENTS

| 4,250,113 A | * | 2/1981 | Nordal et al. ............... 564/153 |
| 5,191,119 A | | 3/1993 | Sovak et al. |
| 5,204,086 A | * | 4/1993 | Willie ......................... 564/153 |
| 5,451,393 A | * | 9/1995 | Liversidge et al. ......... 424/9.45 |
| 5,527,926 A | * | 6/1996 | Ranganathan et al. ...... 549/480 |
| 5,571,941 A | * | 11/1996 | Villa et al. .................. 564/153 |

FOREIGN PATENT DOCUMENTS

| ES | 532390 | 5/1985 |
| WO | 9910854 | 4/1999 |

* cited by examiner

*Primary Examiner*—Shailendra Kumar
(74) *Attorney, Agent, or Firm*—Dickstein, Shapiro, Morin & Oshinsky LLP.

(57) ABSTRACT

The object of the present invention is an industrial process for the purification and removal of residual solvents from iohexol, based on the suspension of crystalline iohexol, eventually containing residual solvents above 100 ppm, in a fluid wherein it has a low solubility, followed by heating, filtration and drying. The process allows the formation of crystalline iohexol with no residual organic residual solvent above 100 ppm and with an increased purity level.

13 Claims, No Drawings

PROCESS FOR THE PREPARATION OF CRYSTALLINE AND SOLVENT FREE IOHEXOL

It is known that non-ionic X-ray contrast media, such as iohexol, present advantages in relation to prior art ionic compounds. All of these products depend on the presence of large quantities of iodine in the molecule to provide an opaque background, allowing their use to visualise internal organs. However, the quantities needed for this purpose are extremely high, being many times higher than those needed for compounds used as medicines. It is normal to inject as much as 200 g of contrast media agent into a patient. For this reason, the above mentioned substances should have extremely low toxicity and minimal interference with the normal functions of the organism. Additionally, the high dosing regime requires the residual solvent content to be as low as possible. Therefore, there is an increasing need to develop manufacturing processes for the production of contrast media of the highest purity.

There exist several methods which can be used to produce high purity bulk pharmaceutical products. Possibly the most efficient method for the production of high purity product is a chromatographic process. However, in the present instance, such a method is difficult to implement given the extremely large quantities of product that are necessary. Chromatographic methods are usually associated with low volume and high value product.

Chemical methods, such as crystallisation or washing of a suspension, are the most suitable but they do not always allow the successful removal of impurities with molecular structures that are very similar to that of the primary product. In the case of iohexol, the most problematic impurities are O-alkylated derivatives. In terms of the molecular configuration in the crystal, the properties of these substances are very similar to those of iohexol, being easily introduced in the crystalline structure, with the consequent difficulty in their removal.

Another general consideration is the fact that the molecules used as X-ray contrast media are extremely soluble, especially in aqueous media, and hence their difficult crystallisation. It is believed that this is due to the high degree of freedom associated with the hydrophilic side chains containing alcohol functions.

The prior art cites various solvent systems considered adequate for the crystallisation of iohexol. The first of these systems comprises the use of butanol, as described in U.S. Pat. No. 4,250,113. In this case, the so-obtained product required subsequent dissolution in water, followed by evaporation to dryness under vacuum, in order to remove the residual butanol from the crystallised product.

U.S. Pat. No. 5,191,119 describes the purification of iohexol using a chromatographic procedure. The product is obtained from a 10% methanol/water eluent mixture by an undisclosed process.

Spanish Patent No. 532,390 describes the crystallisation of iohexol using a mixture of aqueous methanol and isopropanol.

U.S. Pat. No. 5,204,086 states that the most effective method of purification of iohexol is crystallisation from boiling isopropanol, but it was found that only 25–30% of the O-alkylated products could be removed in a single crystallisation. Also, further crystallisations significantly increase the cost of the process.

In addition to the insufficient removal of the O-alkylated products, the inventors of the present invention have verified that the product of this last process contains approximately 1000 ppm of isopropanol. The drying step, even though prolonged, does not allow one to reduce the isopropanol content to below several hundred parts per million. It is to be noted that the iohexol monograph published in the 3rd Edition of the European Pharmacopoeia limits the presence of isopropanol to 100 ppm. The same monograph limits methanol and methoxyethanol contents to 50 and 100 ppm, respectively. The United States Pharmacopeia limits the content of the O-alkylated products to 0.6%.

In the same way, crystallisations from methanol or butanol yield a product which, after prolonged drying, contains several hundred parts per million of the crystallisation solvents.

In order to overcome the problem of high residual solvent content, the procedure which is currently recognized as the most suitable is to dissolve the iohexol in water, followed by freeze-drying or spray-drying, by which the product is obtained as an amorphous solid. An obvious disadvantage of this procedure is the requirement to carry out beforehand purification processes for the removal of impurities, such as the O-alkylated products, followed by the use of extremely expensive equipment and processing.

There is thus a need for a simple chemical process that has the following advantages: to act as a purification process to remove the O-alkylated products; while at the same time giving a product that does not have any residual solvent above 100 ppm.

The present invention accomplishes both of these objectives, with the additional advantage that the final product is crystalline. Crystalline compounds are always preferred by the pharmaceutical industry as they are more stable.

The inventors have found that concentrating an aqueous solution of iohexol followed by the addition of ethanol, yields crystalline iohexol, provided that the temperature is adequate and the amount of water is less than that required to cause complete dissolution. The crystallisation is promoted by the addition of some iohexol crystals. After filtration and drying in a conventional drier, the iohexol thus obtained has an increased purity in relation to that of the starting solution and, unexpectedly, contains an ethanol content below 100 ppm.

The inventors have also found that when fluidising iohexol, containing residual solvent contents above the required limit, at an adequate temperature, in a medium containing another solvent, there is an interchange of such solvents. For the intended use, the obvious substitution solvent is water.

The fluidising agent may eventually be a gas, preferably air or an inert gas, in which case, despite the reduction in the residual solvents there will be no reduction in the other impurities. The use of a solvent or a solvent mixture as fluidising agent allows one to achieve the more general purpose. The interchange agent may eventually be the same as the fluidising agent.

The choice of the fluidising agent and its ratio in relation to the interchange agent and iohexol should be carefully carried out in order that the iohexol dissolution is minimal and there is an adequate dissolution of the impurities to be removed.

A convenient fluidising agent is ethanol due to its low toxicity in relation to other organic solvents. The preferred interchange agent is water and its amount should be less than that required to cause complete dissolution of iohexol.

The procedure of choice is to suspend crystalline iohexol, obtained from any of the known processes and containing a residual solvent content above 100 ppm, in absolute ethanol and water. The suspension is then heated, preferably to reflux, after which it is cooled and the solid filtered. The solid obtained is then dried in a conventional drier.

The iohexol so obtained contains less than 100 ppm of any organic solvent. The content of O-alkylated products decreases by at least 25%, typically by 40%. Additionally, the iohexol is in contrast to the prior art from product with has residual solvent contents below 100 ppm but which is amorphous. The fact that the iohexol of the present invention is crystalline presents various advantages over the prior art amorphous form.

Amorphous iohexol has a non-characteristic melting point: the United States Pharmacopeial Reference Substance starts to melt at 190° C. and the melting is complete at 240° C., whilst the crystalline iohexol melts at 262°–263° C.

Following the general concept of this invention, any expert in the art may, with a reduced number of experiments, optimise the conditions therein indicated or find other suitable solvents for the intended purpose.

The following examples serve to illustrate the present invention and are not, in any way, to be considered as a limitation thereof

EXAMPLE 1

An aqueous solution, weighing 1668.6 g and containing 295.5 g of iohexol with 1.3% of O-alkylated products, was concentrated to a weight of 325.1 g. 1.182 lt of absolute ethanol were added, followed by some iohexol crystals. After reflux, crystallisation occurred. The water content of the reaction mixture was corrected by azeotropic distillation and restoration of the distilled volume with absolute ethanol. After cooling, the product was filtered and dried at 70° C. in a static bed drier. The yield of crystalline iohexol was 246.8 g, which contained 0.55% of O-alkylated products and an ethanol content below 40 ppm. Melting point: 262°–263° C.

EXAMPLE 2

200 g of iohexol containing 0.9% of O-alkylated products and 891 ppm of isopropanol were refluxed in absolute ethanol (1.6 lt) and water (20 ml). After cooling, the product was filtered and dried at 80° C., at an atmospheric pressure, in a static bed drier. The yield of crystalline iohexol was 157 g, which contained 0.5% of O-alkylated products, 71 ppm of isopropanol and 14 ppm of ethanol. Melting point: 257°–263° C.

EXAMPLE 3

20 g of johexol, containing 1.12% of O-alkylated products and 2776 ppm of isopropanol, were refluxed in absolute ethanol (120 ml) and water (2 ml). After cooling, the product was filtered and dried at 70° C. in a static bed drier. The yield of crystalline iohexol was 17.2 g, which contained 0.56% of O-alkylated products, 60 ppm of isopropanol and 67 ppm of ethanol. Melting point: 253–254° C.

What is claimed is:

1. An industrial process for the preparation of crystalline iohexol, with a residual solvent content below 100 ppm, characterised by the fact that ethanol is used in the crystallisation.

2. An industrial process for the purification and removal of residual solvents from iohexol, characterised by the fact that crystalline iohexol, containing residual solvents above 100 ppm, is suspended in ethanol wherein it has low solubility, followed by heating, filtration and drying, thereby allowing the formation of crystalline iohexol with no residual organic solvent above 100 ppm and with an increased purity level.

3. A process according to claim 2, characterised by the fact that an amount of water below that required for the complete dissolution of iohexol is added to the ethanolic suspension fluid.

4. A process according to claim 2, characterised by the fact that the starting crystalline iohexol is obtained by crystallisation from isopropyl alcohol.

5. A process according to claim 1, characterised by the fact that an aqueous solution of iohexol is concentrated, followed by the addition of ethanol and heating to an adequate temperature, in order to crystallise the iohexol.

6. A process according to claim 5, characterised by the fact that the temperature is above 30° C.

7. A process according to claim 1, characterised by the fact that iohexol is crystallised from an ethanol and water solution by reduction of the water content.

8. Crystalline iohexol, characterised by the fact that it does not present any residual solvent above 100 ppm.

9. A process according to claim 6, characterized by the fact that the temperature is reflux.

10. A process according to claim 2, characterized by the fact that the crystalline iohexol containing residual solvents above 100 ppm is suspended in a combination of ethanol and a quantity of water below that required for complete dissolution of the iohexol and the suspension is heated to reflux.

11. A process according to claim 10, characterized by the fact that the ethanol is absolute ethanol.

12. A process according to claim 11, characterized by the fact that the residual solvent comprises isopropyl alcohol.

13. A process according to claim 9, characterized by the fact that the residual solvent comprises isopropyl alcohol.

* * * * *